United States Patent
Edwards et al.

(10) Patent No.: US 7,998,921 B2
(45) Date of Patent: Aug. 16, 2011

(54) METHOD OF REDUCING TOILET ODOR

(75) Inventors: William Edwards, Aiea, HI (US);
Derek Edwards, Chesterton, IN (US);
Frederick E. Edwards, Valparaiso, IN (US)

(73) Assignee: Toilex, LLC, Valparaiso, IN (US)

( * ) Notice: Subject to any disclaimer, the term of this patent is extended or adjusted under 35 U.S.C. 154(b) by 0 days.

(21) Appl. No.: 12/246,821

(22) Filed: Oct. 7, 2008

(65) Prior Publication Data

US 2009/0028748 A1 Jan. 29, 2009

Related U.S. Application Data

(62) Division of application No. 11/419,025, filed on May 18, 2006, now Pat. No. 7,449,441.

(60) Provisional application No. 60/594,915, filed on May 18, 2005.

(51) Int. Cl.
*C11D 17/00* (2006.01)

(52) U.S. Cl. ......... 510/506; 510/191; 510/476; 510/505
(58) Field of Classification Search ............... 510/506
See application file for complete search history.

(56) References Cited

U.S. PATENT DOCUMENTS

| 2003/0008792 A1* | 1/2003 | Shaukat et al. | 510/191 |
| 2003/0068295 A1* | 4/2003 | Rohde et al. | 424/76.1 |

* cited by examiner

*Primary Examiner* — Harold Y Pyon
*Assistant Examiner* — Timothy Chiang
(74) *Attorney, Agent, or Firm* — Hartman & Hartman, P.C.; Gary M. Hartman; Domenica N. S. Hartman

(57) ABSTRACT

A method of eliminating or at least reducing toilet odor by applying a liquid composition directly to the water contained in a toilet bowl prior to use. The liquid composition contains about 60 to about 70 weight percent diethylene glycol monoethyl ether ($CH_2OHCH_2OCH_2CH_2OC_2H_5$), the balance being at least additional constituent, such as fragrances and/or stabilizers. The liquid composition reacts with the water so as to roil in the water, forms a sheen on the surface of the water, and reduces toilet odors during and following usage of the toilet bowl.

4 Claims, No Drawings

METHOD OF REDUCING TOILET ODOR

CROSS REFERENCE TO RELATED APPLICATIONS

This is a division patent application of co-pending U.S. patent application Ser. No. 11/419,025, filed May 18, 2006, which claimed the benefit of U.S. Provisional Application No. 60/594,915, filed May 18, 2005. The contents of these applications are incorporated herein by reference.

BACKGROUND OF THE INVENTION

The present invention generally relates to methods and compositions for eliminating toilet odor by direct application of a composition to the water contained in the toilet bowl prior to use.

A product under the name "Powerful One-Drop" is commercially available from Kobayashi Pharmaceutical Co., Ltd., of Japan for eliminating toilet odor by adding the product to the water in a toilet bowl after use, optionally prior to use. According to the information provided on its packaging, this product contains fragrances, plant extract, and glycol ether (dipropylene glycol monomethyl ether, also known as (2-methoxymethylethoxy)-propanol; $(CH_3(OC_3H_6)_2OH$; CAS Number 34590-94-8). Another product of this type is available from Prelam Enterprises Ltd. of Moncton, New Brunswick, Canada, under the name "Just' a Drop." The ingredients of this product have been described in literature as a plant extract, disinfectant, and perfume.

BRIEF SUMMARY OF THE INVENTION

The present invention provides a method of eliminating or at least reducing toilet odor by applying a liquid composition directly to the water contained in a toilet bowl prior to use. The liquid composition comprises about 60 to about 70 weight percent diethylene glycol monoethyl ether (CH2OHCH2OCH2CH2OC2H5; also known as diglycol monoethyl ether, etc.; CAS No. 111-90-0), the balance being one or more stabilizers and optionally one or more fragrances. According to particular and preferred aspects of the invention, the liquid composition does not contain dipropylene glycol monomethyl ether other than as a possible constituent of the stabilizer(s). The liquid composition appears to react with water, in that droplets of the composition placed in water appear to roil in the water before forming a sheen on the water surface.

When used in an effective amount, typically about two to four droplets, to the water in a typical toilet bowl, the sheen formed by the liquid composition is sufficient to cover essentially the entire surface of the water. Thereafter, toilet odors emanating from the toilet bowl are drastically reduced if not eliminated during and following subsequent toilet usage.

Other objects and advantages of this invention will be better appreciated from the following detailed description.

DETAILED DESCRIPTION OF THE INVENTION

As noted above, the present invention provides a method capable of reducing toilet odors by applying a liquid composition directly to water contained in a toilet bowl prior to use of the toilet bowl. In a preferred embodiment, the liquid composition consists of about 60 to about 70 weight percent diethylene glycol monoethyl ether, at least one stabilizer, and optionally but preferably additional constituents such as fragrances.

Testing has evidenced that the ratio of the diethylene glycol monoethyl ether to the remainder of the constituents is critical. Suitable results have been obtained with the composition formulated to contain 60 to 70 weight percent diethylene glycol monoethyl ether, with the balance fragrances and an effective amount of stabilizer (e.g., about 0.5 weight percent). Compositions containing diethylene glycol monoethyl ether outside this range have not been effective. Optimal results appear to be obtained with the composition containing about 65 weight percent diethylene glycol monoethyl ether, about 34.5 weight percent fragrances, and about 0.5 weight percent of a stabilizer commercially available under the names Optical Bright Benetex OB-EP or Optiblanc ATR Liquid. These stabilizers are believed to contain about 40 to about 50 weight percent dipropylene glycol monomethyl ether (also known as 2-methoxymethylethoxy)-propanol; $(CH_3(OC_3H_6)_2OH$; CAS No. 34590-94-8), about 40 to about 50 weight percent ethoxylated alkyl phenol, and less than 2 weight percent of a coumarin derivative.

Various fragrances can be used in the liquid composition of this invention. Two fragrances successfully used in combination are proprietary fragrances available through WholesaleSuppliesPlus.com (North Royalton, Ohio) under the names "Lavender Breeze" and "Christmas Wreath Yankee Type." In the composition noted above as containing about 65 weight percent diethylene glycol monoethyl ether, about 34.5 weight percent fragrances, and about 0.5 weight percent of a stabilizer, the "Lavender Breeze" and "Christmas Wreath Yankee Type" fragrances constituted about 11.5 and about 23.0 weight percent, respectively, of the total composition. In addition to fragrances, it is foreseeable that other additives could be included in the liquid composition to provide various performance, processing, or economic benefits.

When used in an effective amount, typically about two to four droplets to standing water in a typical toilet bowl, the liquid composition of this invention appears to react with water, presumably from the diethylene glycol monoethyl ether content of the composition, in that droplets of the composition appear to roil in the water (a reaction that is believed not to occur with compositions containing dipropylene glycol monomethyl ether in amounts greater than its use as a possible constituent of the stabilizer). Thereafter, a sheen appears on the water surface. Normal use of the toilet can then proceed, during and after which normal toilet odors are greatly reduced if not eliminated.

While the invention has been described in terms of a preferred embodiment, it is apparent that other forms could be adopted by one skilled in the art. Therefore, the scope of the invention is to be limited only by the following claims.

The invention claimed is:

1. A method of reducing toilet odor, the method comprising the step of applying a liquid composition directly to water contained in a toilet bowl prior to use thereof, the liquid composition comprising of 60 to 70 weight percent diethylene glycol monoethyl ether, the balance of the liquid composition being a stabilizer compound and at least one fragrance, the stabilizer compound constituting about 0.5 weight percent of the liquid composition and containing about 40 to about 50 weight percent dipropylene glycol monomethyl ether, wherein the liquid composition reacts with the water so as to roil in the water, forms a sheen sufficient to cover essentially the entire surface of the water, and reduces toilet odors during and following usage of the toilet bowl.

2. The method according to claim 1, wherein the stabilizer compound further contains about 40 to about 50 weight percent ethoxylated alkyl phenol.

3. The method according to claim 1, wherein the stabilizer compound further contains less than 2 weight percent of a coumarin derivative.

4. The method according to claim 1, wherein the liquid composition consists of about 65 weight percent diethylene glycol monoethyl ether, about 34.5 weight percent of the at least one fragrance, and about 0.5 weight percent of the stabilizer compound.

* * * * *